United States Patent [19]
Marchment

[11] Patent Number: 5,611,788
[45] Date of Patent: Mar. 18, 1997

[54] EYE DROP DISPENSER

[76] Inventor: David Marchment, R.R.3, Site 16C, Compartment 11, Kelowna, British Columbia V1Y 7R2, Canada

[21] Appl. No.: 497,933

[22] Filed: Jul. 5, 1995

[51] Int. Cl.$^6$ .......................... A61H 35/00; A61H 33/04
[52] U.S. Cl. .......................... 604/295; 604/300; 604/301
[58] Field of Search .................................. 604/294, 295, 604/298, 300, 301, 302; 215/228, 295, 305, 11.1; 222/420, 419

[56] References Cited

U.S. PATENT DOCUMENTS

| | | | |
|---|---|---|---|
| 4,685,906 | 8/1987 | Murphy | 604/300 |
| 5,064,420 | 11/1991 | Clarke et al. | 604/295 |
| 5,382,243 | 1/1995 | Mulholland | 604/302 |
| 5,454,476 | 10/1995 | King et al. | 215/305 |

Primary Examiner—David Isabella
Assistant Examiner—David J. Cho
Attorney, Agent, or Firm—George A. Seaby

[57] ABSTRACT

In general, eyedrop dispensers are difficult to use and/or unnecessarily complicated in terms of structure. A relatively simple eyedrop dispenser which can be used with one hand includes a tapering, tubular, soft pliable body with a resilient sleeve at one end thereof for mounting the dispenser on a bottle with a cylindrical neck and an annular flange for mating with an annular groove in the sleeve, the remainder of the body flaring outwardly to a wide end, a flange extending outwardly from the wide end with projections or protuberances on the flange for bearing against the face of the user on either side of an eye and for pushing the lower eyelid downwardly, whereby drops are dispensed accurately into the lower eye.

7 Claims, 4 Drawing Sheets

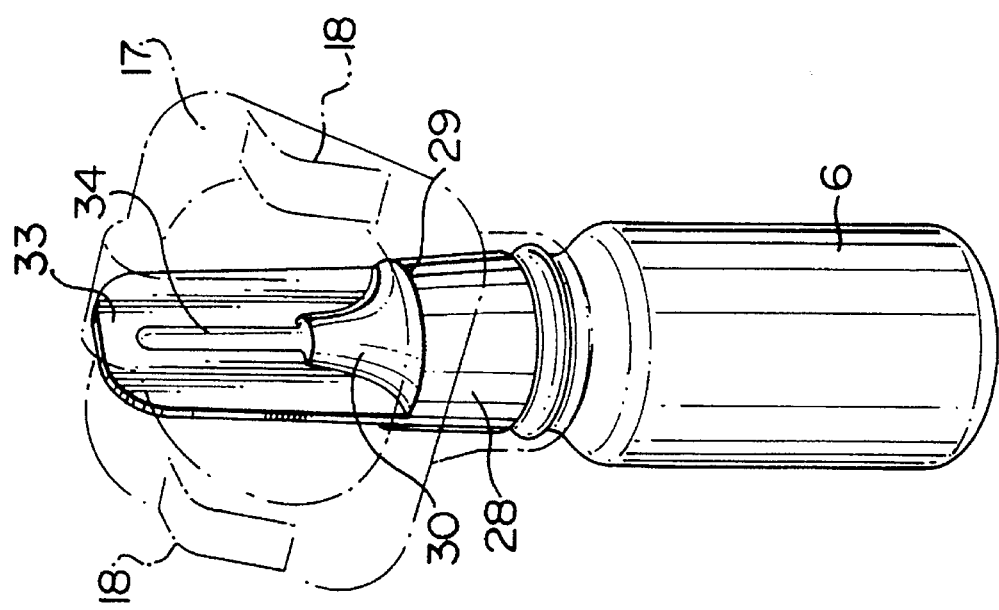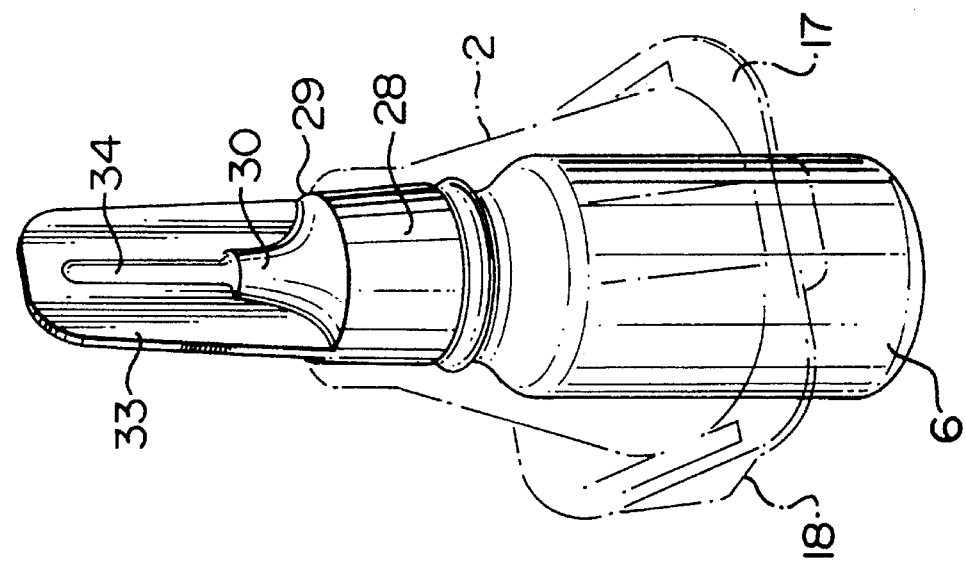

EYE DROP DISPENSER

BACKGROUND OF THE INVENTION

1. Field of the Invention

This invention relates to an eyedrop dispenser, and to an eyedrop dispenser in combination with a bottle for eyedrops.

2. Discussion of the Prior Art

The placing of eyedrops into an eye can be a messy and unpleasant experience. Ideally, the drops should be instilled into the lower eye, specifically into the conjunctival sac or the lower eyelid. When using a conventional eyedrop container, at best, it is difficult to align the nozzle of the container with the preferred area of the eye. Studies have proven that the majority of people (as many as 75%) experience difficulty in placing drops in their eyes.

The patent literature contains many examples of proposed solutions to the problem described above. In this connection reference is made to Canadian Patent No. 1,265,767, which issued to S.J. Bechtle on Feb. 13, 1990, and U.S. Pat. No. 2,898,911, which issued to S. Taylor on Aug. 11, 1959; U.S. Pat. No. 3,872,866, which issued to J. Lelicoff on Mar. 25, 1975; U.S. Pat. No. 4,002,168, which issued to T. Petterson on Jan. 11, 1977; U.S. Pat. No. 4,111,200, which issued to F. Sbarra et al on Sep. 5, 1978; U.S. Pat. No. 4,605,398, which issued to R.S. Herrick on Aug. 12, 1986 and U.S. Pat. No. 5,064,420, which issued to G.P. Clarke et al on Nov. 12, 1991. The fact that few of the patented devices are available in the marketplace is indicative of the fact that they failed to meet the need for an effective eyedrop dispenser. Moreover, some of the devices in question are decidedly complicated, and difficult to use and/or manufacture. Many devices require the use of two hands, one to hold the dispenser and the other to pull down the lower eyelid.

GENERAL DESCRIPTION OF THE INVENTION

An object of the present invention is to provide a relatively simple eyedrop dispenser which is easy to use, i.e. which can be used with one hand while accurately instilling drops in an eye.

Another object of the invention is to provide an eyedrop dispenser, which is soft and pliable for the comfort of the user, and which pulls down the lower eyelid for efficient instillation of eyedrops.

Yet another object of the invention is to provide an eyedrop dispenser which does not necessitate tilting of the head so that the face is more or less horizontal.

Accordingly, the present invention relates to an eyedrop dispenser for use with a bottle including a neck and an annular flange on the neck, said dispenser comprising elongated tapering, tubular body means for mounting on the bottle, said body means including a first, narrow diameter, resilient end, said first end having a diameter smaller than that of the annular flange on the neck of the bottle; annular groove means in said first end for receiving the annular flange when the dispenser is in the use position on a bottle; a second wide diameter end on said body means for covering an area of the face of a user larger than the eye of the user; flange means extending outwardly of the periphery of said second end of said body means, said flange means being inclined with respect to an axis extending longitudinally of said body means through said first end whereby, when said second end of said body means is placed against the face of a user with one side of said flange means proximate the eyebrow, the opposite side of said flange means bears against the face of the user to push the lower eyelid downwardly.

BRIEF DESCRIPTION OF THE DRAWINGS

The invention is described below in greater detail with reference to the accompanying drawings, which illustrate a preferred embodiment of the invention, and wherein:

FIGS. 7 and 8 are perspective views of the bottle of FIG. 4 with the dispenser shown in phantom outline in the storage and use positions, respectively.

For the sake of simplicity, in the following description the ends of the dispenser designated "top and bottom" are the ends of the dispenser when in a storage or non-use position on a bottle.

DESCRIPTION OF THE PREFERRED EMBODIMENT

Figure 3:
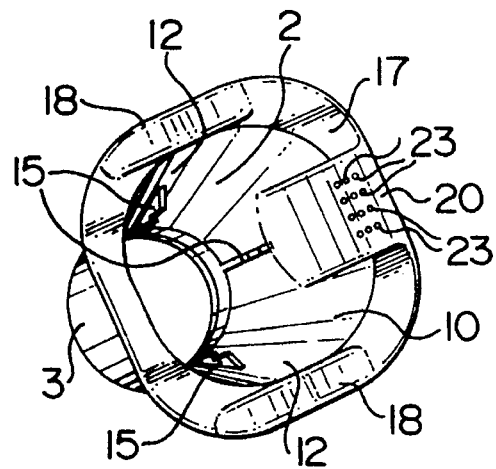
FIG. 3 is a perspective view of the dispenser of FIGS. 1 and 2 from one end thereof.
Figure 1:
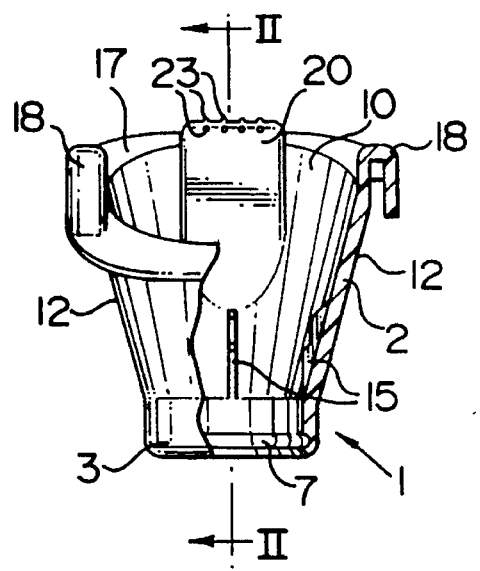
FIG. 1 is a partly sectioned side view of an eyedrop dispenser in accordance with the invention.
Figure 2:
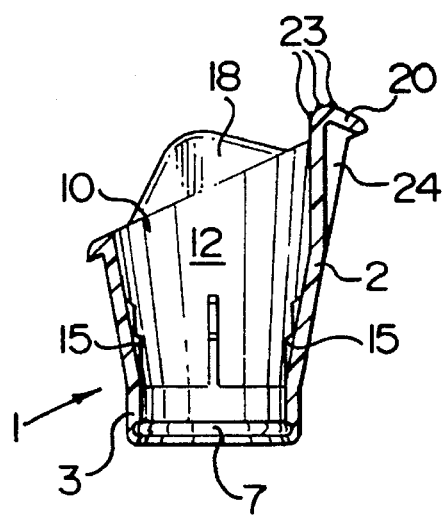
FIG. 2 is a cross section taken generally along line II—II of FIG. 1.
Figure 6:
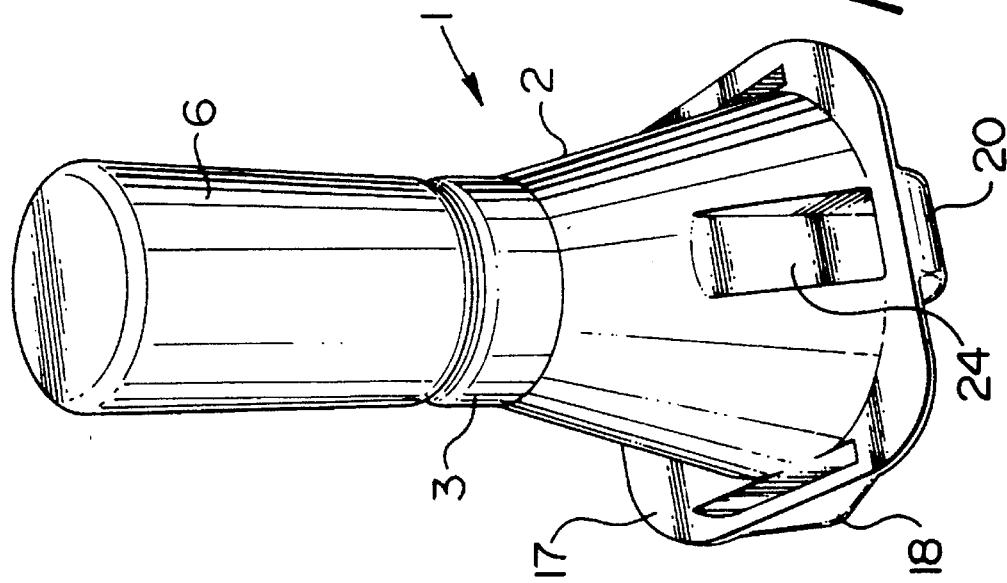
FIGS. 5 and 6 are perspective views of the dispenser of FIGS. 1 to 3 mounted on a bottle in the dispensing position.
Figure 5:
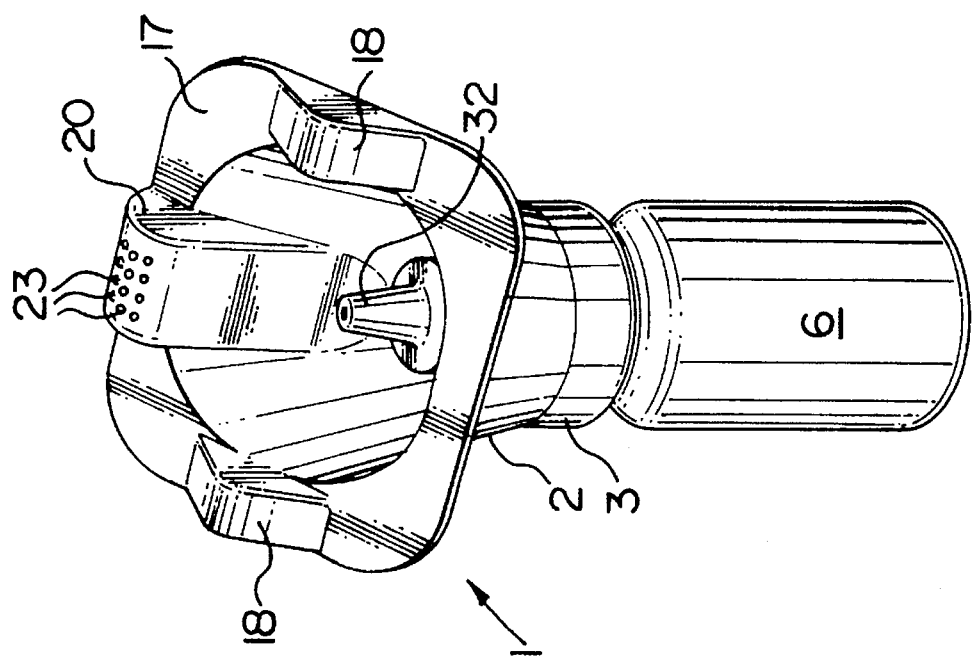

Referring to FIGS. 1 to 3, the eyedrop dispenser, which is generally indicated at 1, includes an elongated, tapering body 2 formed of a soft, pliable, resilient plastic for ensuring comfort when the body is placed against the face of a user. The body 2 includes a short, cylindrical bottom portion or sleeve 3 for mounting on the neck (FIGS. 4 to 7) of an eyedrop containing bottle 6. An annular groove 7 in the sleeve 3 is designed to receive an annular ridge or flange 8 on the neck 4 of the bottle 6 when the dispenser is mounted on the bottle as a preliminary to a drop dispensing operation.

Figure 9:
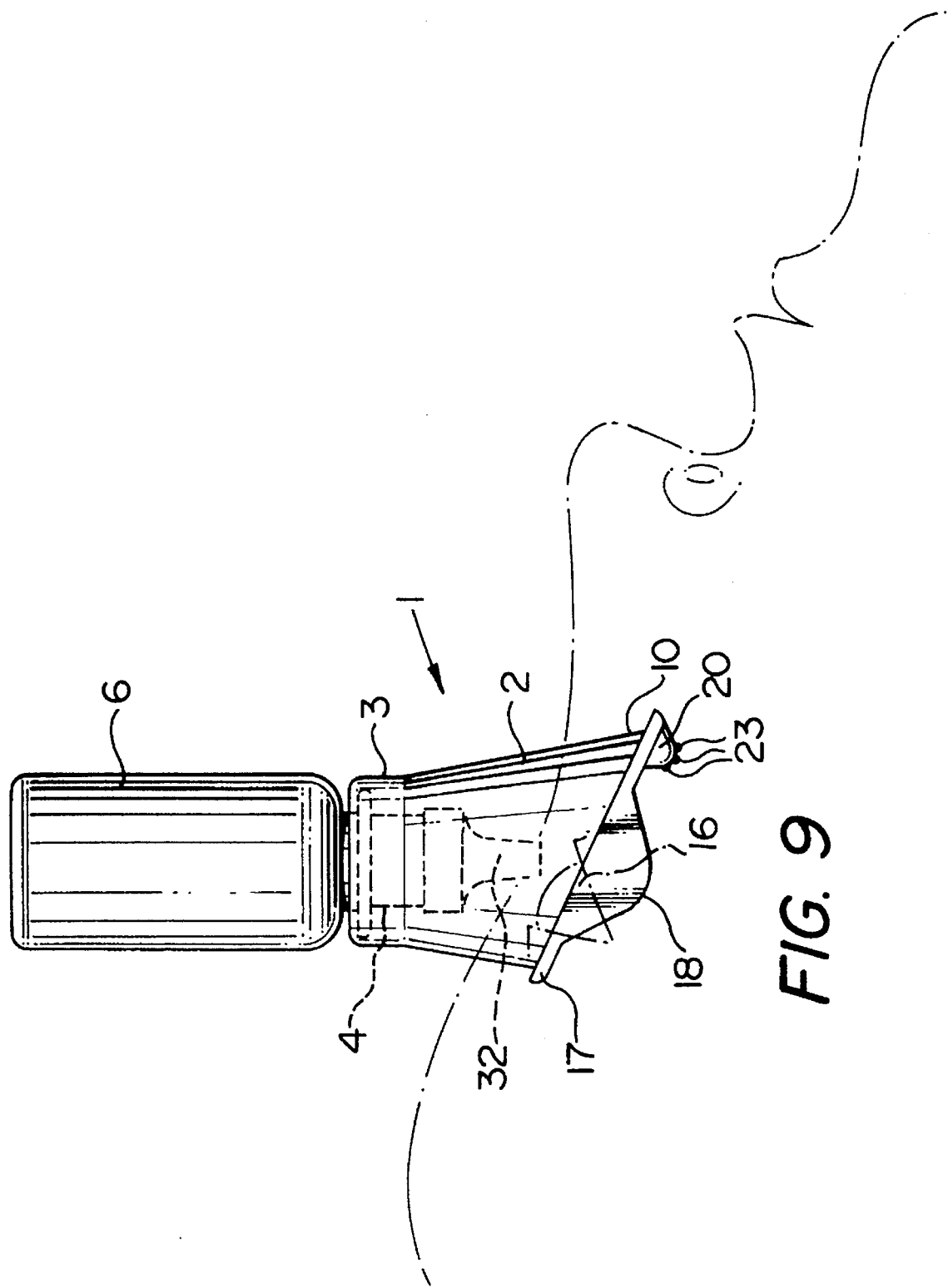
FIG. 9 is a schematic side view of the dispenser of FIGS. 1 to 6 in use.

The remainder or upper portion 10 of the body 2 flares downwardly and outwardly from the upper portion 3, opposite sides 12 therof being symmetrical with respect to a plane extending through the longitudinal axis of the body 2. Four small ribs or vanes 15 extend radially inwardly from the interior of the upper end of the lower portion 10 of the body 2. The ribs 15 have stepped inner free edges for engaging the annular flange 8 on the neck of the bottle when the body 2 is mounted in the storage or non-use position (FIG. 4) on the bottle 6 to limit downward movement of the dispenser on the bottle. While the bottom edge of the body 2 is perpendicular to the longitudinal axis of the body, the top edge of the upper portion 10 is inclined with respect to such longitudinal axis. Thus, as shown in FIG. 9, when the device is placed against the face of a user, the higher end of the what is now the bottom edge of the body 2 is located above the eyebrow of the user and the lower end thereof is located immediately below the eye 16. The inclination of the bottom edge of the body 2 is chosen so that drops can be instilled with minimum tilting of the head.

A generally rectangular flange 17 extends outwardly from the periphery of the wide top edge of the body 2. The flange 17 has rounded corners and is symmetrical with respect to the longitudinal axis of the body 2. A pair of bulbous, generally triangular projections 18 are provided on opposite, inclined sides of the flange 17 for engaging the face of a user on each side of the eye 16. As best shown in FIG. 7, the projections 18 have a convex or rounded outer end for smooth contact with the skin. A third projection 20 is provided on the center of the lower side (in the use position) of the flange 17. The projection 20 extends from a point immediately beneath one of the ribs 15 downwardly and inwardly, and then curves sharply outwardly to the outer edge of the flange 17. A plurality of small bumps or pimples 23 are provided on the bottom edge of the projection 20 for improving engagement with the skin. The purpose of the projection 20 is to push down the lower eyelid (the conjunctival sac) to ensure that eyedrops dispensed from the bottle 6 fall into the sac and hit the lower eyeball. The bulk of the projection 20 is formed by a generally rectangular recess 24 (FIGS. 2 and 6) in the outer surface of the upper portion 10 of the body 2.

When packaged in a cardboard container 25 (FIG. 4) the dispenser 1 is inverted on the bottle 6, resting on the shoulder 26 of the bottle 6 and surrounding a resilient, cylindrical sleeves defining the lower end 28 of a cap 29. As mentioned above, the stepped ribs 15 engage the flange 8 for limiting downward movement of the dispenser 1 on the bottle 6. In order to use the dispenser 1, the cap 29 is removed from the bottle 6, the dispenser 1 is inverted, and the upper portion or sleeve 3 is snapped over the flange 8, so that the latter enters the groove 7. The cap 29 includes a tapering, generally conical upper end 30 for surrounding the tapering dispensing nozzle 32 (FIG. 5) on the upper end of the bottle 6. A thin, planar tab 33 extends upwardly from the upper end 30 for facilitating removal of the cap 29. The tab 33 is reinforced by a central, vertically extending rib 34.

Figure 4:
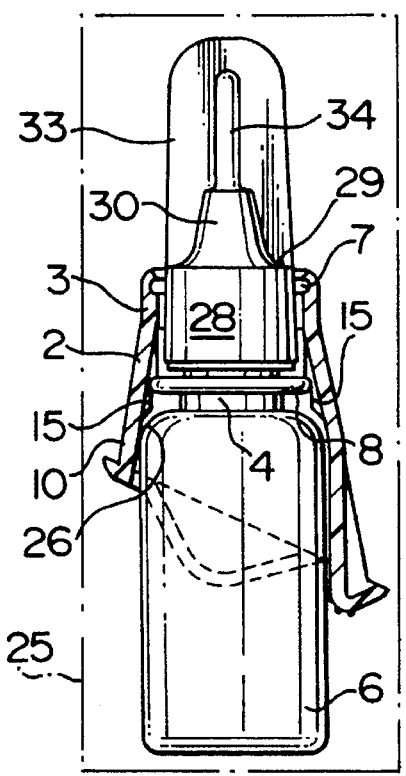
FIG. 4 is a cross-sectional view of the dispenser of FIGS. 1 to 3 mounted on a bottle in the storage or non-use position.

As will be readily apparent from FIGS. 4 to 8, the dispenser and bottle combination are delivered to the consumer with the dispenser oriented in such a manner than the wide discharge end surrounds the bottle 6 (FIGS. 4 and 7). In order to prepare the device for dispensing, the dispenser 1 is removed from the bottle 6 inverted and re-attached to the bottle 6, so that the discharge end is located above the nozzle 32 of the bottle. The cap 29 is removed either before or after removal of the dispenser from the bottle 1. The use of an elongated tab 33 makes it easy to remove the cap 29. With the dispenser 1 in position (FIGS. 5 and 8) the head is tilted back, and the dispenser and bottle are located over the eye 16 (FIG. 9). By exerting slight downward pressure, the lower eyelid is moved downwardly so that drops are dispensed into the bottom of the eye 16 upon squeezing the bottle 6.

I claim:

1. An eyedrop dispenser for use with a bottle including a neck and an annular flange on the neck, said dispenser comprising elongated tapering, tubular body means for mounting on the bottle, said body means including a first, narrow diameter, resilient end, said first end having a diameter smaller than that of the annular flange on the neck of the bottle; annular groove means in said first end for receiving the annular flange when the dispenser is in the use position on a bottle; a second wide diameter end on said body means for covering an area of the face of a user larger than the eye of the user; flange means extending outwardly of the entire periphery of said second end of said body means, said flange means being inclined with respect to an axis extending longitudinally of said body means through said first end whereby, when said second end of said body means is placed against the face of a user with one side of said flange means proximate the eyebrow, the opposite side of said flange means bears against the face of the user; and first projection means extending longitudinally outwardly from said opposite side of said flange means for forcing the lower eyelid downwardly away from the eye of a user when the dispenser is in the use position, whereby the dispensing of liquid beneath the lower eyelid is facilitated.

2. The eyedrop dispenser of claim 1, including a plurality of small, spaced apart protuberance means on said first projection means facilitating gripping of the skin by said first projection means.

3. The eyedrop dispenser of claim 2, including second and third projection means on sides of said flange means at right angles to said opposite side of the flange means for supporting the dispenser above the eye of a user.

4. The eyedrop dispenser of claim 3, including rib means in said body means for engaging said annular flange to limit downward movement of the dispenser on a bottle in the storage position.

5. An eyedrop dispenser and bottle combination comprising a bottle including neck means and first annular flange means on the neck, said dispenser comprising elongated tapering, tubular body means for mounting on the bottle, said body means including a first, narrow diameter, resilient end, said first end having a diameter smaller than that of the first flange means on the neck of the bottle; annular groove means in said first end for receiving the first flange means when the dispenser is in the use position on a bottle, a second wide diameter end on said body means for covering an area of the face of a user larger than the eye of the user; second flange means extending outwardly of the entire periphery of said second end of said body means, said second flange means being inclined with respect to an axis extending longitudinally of said body means through said first end whereby, when said second end of said body means is placed against the face of a user with one side of said second flange means proximate the eyebrow, the opposite side of said second flange means bears against the face of the user; and first projection means extending longitudinally outwardly from said opposite side of said flange means for forcing the lower eyelid downwardly away from the eye of a user when the dispenser is in the use position; whereby dispensing of liquid beneath the lower eyelid is facilitate.

6. The combination of claim 5, wherein said bottle includes dispensing nozzle means and cap means, said cap means including resilient, cylindrical sleeve means for mounting on the neck means of the bottle above said first flange means; said sleeve means being covered by said first end of said body means when the dispenser is in the storage position on the bottle; and tab means extending upwardly from said sleeve means facilitating gripping of the cap means for removal of the cap means from the bottle.

7. The combination of claim 6, wherein said tab means includes thin plate means extending upwardly from said sleeve means; and reinforcing rib means extending longitudinally of said plate means.

* * * * *